United States Patent [19]

Clark, Jr. et al.

[11] Patent Number: 5,290,953
[45] Date of Patent: Mar. 1, 1994

[54] PROCESS FOR PRODUCING SULFOLANE COMPOUNDS

[75] Inventors: Earl Clark, Jr.; Jimmie J. Straw, both of Bartlesville, Okla.

[73] Assignee: Phillips Petroleum Company, Bartlesville, Okla.

[21] Appl. No.: 46,708

[22] Filed: Apr. 16, 1993

[51] Int. Cl.$^5$ .............................. C07D 333/48
[52] U.S. Cl. ........................ 549/87; 549/66; 549/67
[58] Field of Search .................... 549/87, 66, 67

[56] References Cited

U.S. PATENT DOCUMENTS

| | | | |
|---|---|---|---|
| 3,417,103 | 12/1968 | Warner | 260/332.1 |
| 3,514,469 | 5/1970 | Phillips et al. | 260/332.1 |
| 3,622,598 | 11/1971 | Willis | 260/332.1 |
| 3,998,845 | 12/1976 | Goldstein et al. | 260/332.1 |
| 4,275,218 | 6/1981 | Huxley et al. | 549/87 |
| 5,030,737 | 7/1991 | Nash | 549/87 |

Primary Examiner—Richard L. Raymond
Attorney, Agent, or Firm—Lucas K. Shay

[57] ABSTRACT

A process for producing sulfolane compounds is provided which comprises: (1) contacting a conjugated diene with sulfur dioxide under conditions sufficient to synthesize a sulfolene compound whereby a mixture of the sulfolene compound and impurities comprising unreacted sulfur dioxide is produced; (2) transferring the mixture, at a temperature in the range of about 55° C. to about 85° C., to an impurities removal reactor containing a solvent; (3) removing the impurities under an elevated pressure to produce an impurities-reduced sulfolene compound; (4) transferring the impurities-reduced sulfolene compound to a hydrogenation reactor; (5) contacting said impurities-reduced sulfolene compound with hydrogen, in the presence of a hydrogenation catalyst, under conditions sufficient to produce a sulfolane compound; and (6) optionally recovering said sulfolane compound.

16 Claims, No Drawings

PROCESS FOR PRODUCING SULFOLANE COMPOUNDS

FIELD OF THE INVENTION

This invention relates to a process for producing sulfolane compounds from a conjugated diene and sulfur dioxide.

BACKGROUND OF THE INVENTION

Sulfolane compounds are useful in a variety of industrial applications such as, for example, in pesticidal compositions, intermediates in the production of other organic chemicals, selective solvents to separate aromatic compounds from petroleum fractions, and selective solvents in alkylation of olefins.

Sulfolane compounds are generally prepared by catalytic hydrogenation of the corresponding sulfolene compounds. The sulfolene compounds are prepared by the reaction of a conjugated diene such as, for example, 1,3-butadiene, and sulfur dioxide at elevated temperatures.

However, the sulfolene compounds thus-produced are generally unstable and tend to decompose at mildly elevated temperatures into an unsaturated organic compound and sulfur dioxide. Furthermore, when the sulfolene compounds are used to prepare the corresponding sulfolane compounds by catalytic hydrogenation, the initiation of hydrogenation reaction may also increase the temperature enough to result in some decomposition of the sulfolene. Some of these decomposed products polymerize and the resulting polymer coats the hydrogenation catalyst significantly reducing its activity. Moreover, unreacted sulfur dioxide and the sulfur dioxide obtained from decomposition of sulfolene compounds also interfere with the subsequent catalytic hydrogenation. These sulfur dioxides must be removed or substantially reduced.

Processes have been developed for inhibiting the formation of polymers and reduction of sulfur dioxide in the production of sulfolane compounds. For example, amines have been used as inhibitors in reducing the amount of polysulfone polymer formation. Oxidizing agents have been used to reduce sulfur dioxide and other impurities. However, there is an ever present need to develop still more effective methods of reducing the polymer formation, the removal of sulfur dioxide and impurities, and the hydrogenation process so that the amount of hydrogenation catalyst used can be reduced and the production of sulfolane compounds can be greatly improved.

SUMMARY OF THE INVENTION

An object of the invention is to reduce the formation of sulfone polymer during the preparation of sulfolane compounds. Another object of the invention is to remove dissolved sulfur dioxide from the sulfolene compounds. A further object of the invention is to reduce the amount of hydrogenation catalyst used in converting sulfolene compounds to corresponding sulfolane compounds. Still another object of the invention is to develop a process to improve the productivity of sulfolane compounds produced. An advantage of the invention is the reduction of the formation of sulfone polymer. Other objects, features and advantages will become more apparent as the invention is more fully disclosed hereinbelow.

According to the present invention, a process for producing sulfolane compounds is provided which comprises: (1) contacting a conjugated diene with sulfur dioxide under conditions sufficient to synthesize a sulfolene compound whereby a mixture of the sulfolene compound and impurities comprising unreacted sulfur dioxide is produced; (2) transferring the mixture, at a temperature in the range of about 55° C. to about 85° C., to an impurities removal reactor containing a solvent; (3) removing the impurities under an elevated pressure to produce an impurities-reduced sulfolene compound; (4) transferring the impurities-reduced sulfolene compound to a hydrogenation reactor; (5) contacting said impurities-reduced pure sulfolene compound with hydrogen, in the presence of a hydrogenation catalyst, under conditions sufficient to produce a sulfolane compound; and (6) optionally recovering said sulfolane compound.

DETAILED DESCRIPTION OF THE INVENTION

The term "sulfolene" (sometimes referred to as "sulfolenes" or "sulfolene compounds") as employed herein is defined in U.S. Pat. No. 3,622,598, which is incorporated herein by reference. This term includes substituted and unsubstituted 3-sulfolenes and 2-sulfolenes. The preferred sulfolene compound used in this invention is unsubstituted 3-sulfolene, which is commercially available and is produced by reaction of 1,3-butadiene and sulfur dioxide. The terms "sulfolane" and "sulfolane compounds" are also defined in U.S. Pat. No. 3,622,598.

The sulfolene compounds can be prepared by reacting sulfur dioxide with a conjugated diene having the structural formula R—C(R)=C(R)—C(R)=C(R)—R wherein each R can be the same or different and is selected from the group consisting of hydrogen and various organic and/or inorganic radicals which do not interfere with the reaction to produce the sulfolene compound or the subsequent hydrogenation reaction to produce the corresponding sulfolane compound. Inorganic radicals which are suitable include the halogens, hydroxyl groups, and mixtures thereof. Organic radicals which are preferred include hydrocarbyl substituents having 1 to 8 carbon atoms per radical.

A presently preferred class of starting materials comprises the conjugated dienes of the structural formula indicated above where each R is individually selected from the group consisting of hydrogen, alkyl, alkenyl, aryl, cycloalkyl, cycloalkenyl, aralkyl, alkaryl, alkylcycloalkyl, and combinations thereof. The total carbon content of the conjugated diene is in the range of 4 to 18.

Representative examples of the conjugated dienes include, but are not limited to, 1,3-butadiene, 2-methyl-1,3-butadiene (isoprene), 2,3-dimethyl-1,3-butadiene, 2,3-diethyl-1,3-butadiene, 3,4-dimethyl-2,4-hexadiene, 2,4-dodecadiene, 2-methyl-1,3-hexadiene, 4-ethyl-1,3-hexadiene, 1-cyclopentyl-1,3-pentadiene, 1-(1-cyclohexene-1-yl)-1,3-butadiene, 2-phenyl-1,3-butadiene, 3-benzyl-1,3-pentadiene, 3-p-tolyl-1,3-pentadiene, and their homologues and analogues, and mixtures thereof. Also, suitable substituted derivatives of the above and like polyenes may be reacted with sulfur dioxide to form the desired mono-sulfones, examples of such substituted polyenes being 2-chloro-1,3-butadiene, 2-methyl-3-chloro-1,3-butadiene, 1-cyano-1,3-butadiene, and mixtures thereof.

Examples of representative sulfolene compounds include, but are not limited to, 2-methyl-3-sulfolene, 2-sulfolene, 3-sulfolene, 3-methyl-2-sulfolene, 3-methyl-3-sulfolene, 2-methyl-3-sulfolene, 2,4-dimethyl-2-sulfolene, 2,4-dimethyl-3-sulfolene, 3-ethyl-3-sulfolene, and mixtures thereof.

The term "reactor" used herein is referred to as, unless otherwise indicated, reaction vessel or vessels that can be properly employed in chemical reactions. The choice of a suitable reactor is generally a matter of preference to one ordinarily skilled in the art.

The first step of the process, according to the present invention, is the contacting of a conjugated diene with sulfur dioxide either in the presence or in the absence of a solvent. It can be either a continuous or a batch operation. The molar ratio of sulfur dioxide to the conjugated diene is in the range of from about 1:1 to about 2:1, preferably about 1:1 to about 1.5:1, and most preferably 1:1 to 1.2:1. The temperature of the reaction is generally in the range of from about 50° C. to about 150° C., preferably about 60° C. to about 120° C., and most preferably from 65° C. to 80° C. The pressure of the reaction vessel is generally in the range of about 10 psig to about 500 psig, preferably about 20 psig to about 300 psig, and most preferably 30 psig to 120 psig.

The solvent suitable for use in the present invention is selected from the group consisting of water, an alcohol, a sulfone, an organic amide, and mixtures thereof. Suitable alcohols include, but are not limited to, methanol, ethanol, propanol, isopropanol, butanol, pentanol, and mixtures thereof. Suitable sulfone solvents include, but are not limited to, sulfolane, 2-methyl sulfolane, 3-methyl sulfolane, 3-ethyl sulfolane, and mixtures thereof. Suitable organic amide solvents include, but are not limited to, N-methyl-2-pyrrolidone, N,N'-dimethylformamide, and mixtures thereof. The weight ratio of the solvent, if present, to the conjugated diene is generally in the range of about 0.05:1 to about 1,000:1, preferably 0.5:1 to 10:1.

The order of addition of reactants to the reaction vessel is not important. Generally, the conjugated diene is added to the reaction vessel which already contains the sulfur dioxide to form a reaction mixture. The reaction mixture is allowed to react for a sufficient time, generally about 2 hours to about 24 hours, to allow substantial completion of the reaction to produce a reaction mixture comprising the sulfolene compound.

Upon the desired completion of the reaction, a molten reaction effluent is transferred to an impurities removal vessel (sometimes referred to as a sulfur dioxide removal vessel) which contains a solvent. The scope of the solvent is the same as described above in the first step of the process. The amount of solvent required is a sufficient amount to provide a fluid solution and the weight ratio of the solvent to the sulfolene is generally in the range of about 1:1 to about 1:20. Water is the presently preferred solvent because it promptly decreases the freezing point of the molten sulfolene compound produced in the first step so that decomposition of the sulfolene compound is minimized. The temperature of the molten reaction mixture and the solvent in the removal reactor is maintained at about 55° C. to about 85° C., preferably about 58° C. to about 80° C., and most preferably 60° C. to 76° C. to minimize the decomposition of sulfolene and the formation of undesirable polymers.

After completion of the transfer, impurities including unreacted sulfur dioxide and the sulfur dioxide produced as a result of decomposition of the sulfolene compounds where the sulfur dioxide may be dissolved in the solvent employed are removed by sparging an inert gas to the contents in the removal vessel, under a pressure in the range of about 5 psig to about 500 psig, preferably about 10 psig to about 300 psig, and most preferably 20 psig to 100 psig. The inert gas is generally sparged at a rate in the range of about 1 to about 100 standard cubic feet per hours (scfh), preferably about 1 to about 50 scfh, and most preferably 1 to 10 scfh. The time required for substantially removing the sulfur dioxide varies, depending on the concentration of the sulfur dioxide and the pressure applied, and is generally about 10 minutes to about 10 hours. The temperature for removal of the sulfur dioxide is generally in the range of about 25° C. to about 100° C., preferably about 35° C. to about 80° C., and most preferably 45° C. to 70° C. Though it is not necessary to stir the reaction mixture during the sulfur dioxide removal, a mechanical mixing, such as stirring, of the reaction mixture can be used to facilitate the removal of sulfur dioxide.

Upon removing substantially all sulfur dioxide, a sulfolene compound having substantially reduced sulfur dioxide and other volatile impurities is produced. The sulfolene compound is thereafter transferred to a hydrogenation reactor followed by addition of a suitable hydrogenation catalyst. Suitable catalysts include any of those known in the art to be useful in the catalytic hydrogenation of sulfolenes to sulfolanes. A preferred class of hydrogenation catalysts are those which comprise the metal hydrogenation catalysts, such as those containing or consisting of nickel, cobalt, copper, platinum, palladium or mixtures of these metals with themselves or with other metals such as iron, zinc, chromium, cadmium, and mixtures thereof. These metals may be used in finely divided form such as, for example, Raney nickel, or may be suitably supported on a support such as kieselguhr, aluminum oxide, and diatomaceous earth. These catalysts can be prepared in any suitable manner known to one skilled in the art. The amount of catalyst utilized will vary with the catalyst but will generally be in the range of about 0.1 to about 20 weight percent based on the weight of sulfolene compounds to be hydrogenated.

According to the present invention, the total hydrogenation catalyst required is added in about 2–10 increments to the hydrogenation reactor containing the sulfolene compounds. Every addition represents about 10% to about 50% of the total hydrogenation catalyst required. The total hydrogenation catalyst required is the amount of catalyst necessary to substantially hydrogenate all sulfolene compounds in the hydrogenation reactor. This is done by monitoring the hydrogen uptake. Hydrogen can be constantly introduced into the hydrogenation reactor and monitored by heat release or by pressurizing the reactor up and watching the pressure decrease. Additional catalyst is added when the hydrogen uptake stops or slows down significantly.

The hydrogenation of the sulfolene compounds is carried out by the conditions well known to one skilled in the art. An example is disclosed in U.S. Pat. No. 3,622,598, which is incorporated herein by reference.

Following completion of the hydrogenation reaction, the sulfolane compounds can be recovered by conventional procedures. Generally, the reaction gases are vented from mixtures and then the reaction mixture is filtered to remove the spent hydrogenation catalyst followed by fractionation of the filtered reaction mixture to remove solvent and unreacted sulfolene compounds.

The following examples are presented to further illustrate the invention and are not to be construed to unduly limit the scope of the invention. All reactors or vessels employed in the examples were 2 gallons in volume and equipped with an electrical heating jacket, cooling coils, a mechanical stirrer, baffles, inlets and outlets, and appropriate temperature controls.

EXAMPLE I

This is a comparative example showing a conventional process for preparing sulfolane compounds.

The runs were carried out as follows. A 2 gallon stainless steel reactor which contained a heel of 4750 grams of sulfolene at 74° C. was charged with 4.2 g of dimethylamine. Sulfur dioxide (1412 g or 22.06 moles) and 1,3-butadiene (1135 g or 20.02 moles) were pumped in at a rate of about 4 to 6 grams per minute while maintaining operating temperature with an external electric heater. The pressure during the above feedstock addition increased to about 160 psig (1102 kPa) by the end of the butadiene addition (e.g., 3.0 hours). The reaction mixture was kept at 74° C. with stirring for 7 to 24 hours while the pressure slowly decreased to about 80 psig (551 kPa).

The reaction mixture was then transferred, using a dip tube, to an impurities removal vessel containing 1000 g of water at 50° C., leaving a heel of 4750 g of sulfolene.

A 100 mm Hg vacuum was applied to the impurities removal reactor for 2 to 6 hours, with continuous mixing to remove most of the sulfur dioxide, while the reactor temperature was maintained at 50° C. The final sulfur dioxide concentration was 100 to 500 ppm determined by iodimetric titration with starch as indicator. Iodimetric titration was carried out by first weighing a sample (1.5 g) into an earlenmyer flask containing 75 ml deionized water. An aliquot (0.25 ml) of starch indicator solution (prepared by heating 4 g soluble starch, 40 g sodium chloride and 200 ml deionized water at boiling with stirring for 2-3 minutes followed by cooling to 25° C.) was added to the flask. The solution in the flask was then titrated with 0.01N iodine to the starch/iodine end point. Concentration of sulfur dioxide was calculated as: ppm $SO_2$ = ml iodine $\times$ normality iodine $\times$ 32.035 $\times$ 1,000.

The $SO_2$-reduced sulfolene/water mixture was transferred to a hydrogenation reactor prior to adding catalyst. Raney nickel catalyst (150 g) was weighed out on a scale, kept wet to prevent it from rapidly oxidizing and charged to the hydrogenation reactor. The reactor was pressured to 400 psig with hydrogen. Hydrogen uptake was monitored by pressure decrease. When the pressure had decreased to 200 psig, the reactor was charged back with hydrogen to 400 psig. When the pressure ceased to fall, the hydrogenation of sulfolene was considered complete. Since the hydrogenation heat of reaction is 32.1 Kcal per gram mole, the reactor medium was maintained at 50° C. by internal cooling coils with cool water. Total sulfolane produced was about 2000 g. Several runs were made by the conventional process which produced sulfone-containing polymer as high as 59.3 g per batch.

EXAMPLE II

This example illustrates one of the invention features by transferring the reaction mixtures produced in the 2 gallon reactor (Example I) at 75° C. to the impurities removal vessel (Example I).

The runs were carried out the same as those described in Example I with the exception that the temperature of the transfer of the reaction mixture containing sulfolene from the butadiene-$SO_2$ reactor to impurities removal vessel was 75° C. As shown in Table I, the polymer produced was greatly reduced by transferring at 75° C. (run 2) when compared to the transfer at temperature of 50° C. (run 1).

TABLE I

| | Sulfone-Polymer Reduction by Invention Process | |
|---|---|---|
| Run No. | Transferring Temperature (°C.) | Polymer (g) |
| 1[a] | 50 | 39.0 |
| 2[b] | 75→50 | 20.8 |

[a]The weight of polymer recovered in the impurities removal reactor was an average of six runs.
[b]Inventive run: the temperature for transferring the reaction mixture was 75° C., then the temperature of the contents in the impurities removal reactor was lowered to 50° C.; the polymer produced was an average value of twenty runs (two runs produced less than 7.9 g of sulfone-containing polymer).

EXAMPLE III

This example shows another feature of the present invention whereby the sulfur dioxide was removed by an elevated pressure, i.e. greater than atmospheric pressure.

The runs were carried out the same as those described in Example I except that sulfur dioxide was removed by maintaining an elevated pressure to the impurities removal vessel as noted in Table II. The results of sulfur dioxide removal is shown in Table II.

TABLE II

| | Sulfur Dioxide Removal from Sulfolene Mixture[a] | | | |
|---|---|---|---|---|
| | | Time | $SO_2$ (ppm) | |
| Run No. | Pressure | (hr) | Initial | Final |
| 11 | 0 psig | 3 | 21966 | 3912 |
| 12[b] | 30→50 psig | 3 + 3 | 22246 | 1275 |
| 13 | 50 psig | 1.5 + 3.5 | 32933 | 936 |
| 14 | 50 psig | 4 | 2799 | 208 |
| 15 | 50 psig | 4 | 2947 | 1321 |
| 16[c] | 100→75 mm Hg | 2 + 2 | 38061 | 215 |
| 17[c] | 100→75 mm HG | 2 + 2 | 45266 | 2052 |
| 18 | 100 mm HG | 4 | 19479 | 986 |
| 19 | 100 mm HG | 4 | 24769 | 1046 |
| 20 | 100 mm HG | 2 | 5776 | 148 |
| 21 | 100 mm HG | 4 | 11620 | 848 |
| 22 | 100 mm HG | 4 | 16338 | 507 |
| 23 | 100 mm HG | 4 | 19135 | 178 |

[a]All runs were carried out by sparging $N_2$ gas at 3 standard cubic feet per hour (scfh) except run 13 in which the $N_2$ sparging was 3 scfh in the first 1.5 hours and then shifted up to 5 scfh. All runs were done with water as solvent except runs 15 and 17 were done with sulfolane as solvent.
[b]Run 12 was done at 30 psig pressure for 3 hours followed by increasing to 50 psig for another 3 hours.
[c]Runs 16-17 were done at 100 mm Hg vacuum for 2 hours followed by decreasing to 75 mm Hg vacuum for an additional 2 hours.

The results shown in Table II indicate that under atmospheric pressure (run 11), very high $SO_2$ concentration (3912 ppm) remained in the sulfolene-containing mixture. The $SO_2$ concentration was substantially reduced by the invention process (runs 12-15). The final $SO_2$ concentration in the inventive runs were comparable to those obtained by conventional processes (runs 16-23).

EXAMPLE IV

This example illustrates yet another feature of the invention by adding small quantities of hydrogenation catalyst in several increments.

The runs were carried out the same as those described in Example I except that a small quantity of Raney nickel was initially added to the hydrogenation reactor. When there was no hydrogen uptake, i.e., the pressure did not decrease any further with time, more Raney nickel (in small quantity) was added to the reactor to restart the hydrogenation reaction. The quantity and number of increments and the results are noted in Table III. Runs 101-108 were control runs in which the amount of Raney nickel initially added to the hydrogenation reactor was more than 50% of total catalyst required for the hydrogenation. Although runs 101 and 106 had less than 50% of total Raney nickel present initially in the hydrogenation reactor, the first two increments were more than 71% of total catalyst required. Runs 109-128 were inventive runs in which the amount of Raney nickel present initially in the reactor was less than 50% of total catalyst required with run 109 as an exception.

TABLE III

Hydrogenation of Sulfolene to Sulfolane

| Run No. | Increment (g) | Total Catalyst (g) | $SO_2^a$ (ppm) | $Ni/SO_2^b$ (g) | Batch Wt (g) | $Ni/g$ Sulfolene$^c$ |
|---|---|---|---|---|---|---|
| 101 | 73 + 72 + 25 | 170 | 383 | 0.444 | 1358 | 0.125 |
| 102 | 75 + 30 | 105 | 210 | 0.500 | 590 | 0.178 |
| 103 | 75 + 30 | 125 | 786 | 0.159 | 1981 | 0.063 |
| 104 | 80 + 20 | 100 | 140 | 0.714 | 1783 | 0.056 |
| 105 | 80 + 50 + 20 | 150 | 326 | 0.460 | 2423 | 0.062 |
| 106 | 75 + 50 + 50 | 175 | 288 | 0.608 | 1046 | 0.167 |
| 107 | 80 + 25 + 25 | 130 | 820 | 0.159 | 2035 | 0.064 |
| 108 | 100 + 30 | 130 | 711 | 0.183 | 2160 | 0.060 |
| 109 | 50 + 30 | 80 | 1715 | 0.047 | 1901 | 0.042 |
| 110 | 40 + 20 + 20 | 80 | 851 | 0.094 | 1545 | 0.052 |
| 111 | 30 + 50 | 80 | 930 | 0.086 | 2130 | 0.038 |
| 112 | 30 + 25 + 25 + 25 | 105 | 1150 | 0.091 | 2087 | 0.050 |
| 113 | 20 + 30 + 20 | 70 | 133 | 0.526 | 2019 | 0.035 |
| 114 | 30 + 50 + 50 | 130 | 1281 | 0.101 | 2110 | 0.062 |
| 115 | 30 + 50 | 80 | 314 | 0.255 | 2040 | 0.039 |
| 116 | 30 + 50 + 10 | 90 | 280 | 0.321 | 1881 | 0.048 |
| 117 | 30 + 50 | 80 | 55 | 0.145 | 1957 | 0.041 |
| 118 | 30 + 50 | 80 | 475 | 0.168 | 2108 | 0.038 |
| 119 | 30 + 50 | 80 | 219 | 0.365 | 1826 | 0.044 |
| 120 | 30 + 50 + 10 | 90 | 834 | 0.108 | 1850 | 0.049 |
| 121 | 30 + 50 + 20 | 100 | 1110 | 0.090 | 1803 | 0.055 |
| 122 | 30 + 50 + 30 | 110 | 1201 | 0.092 | 1932 | 0.057 |
| 123 | 30 + 50 + 30 | 110 | 906 | 0.121 | 1959 | 0.056 |
| 124 | 30 + 50 + 30 | 110 | 296 | 0.372 | 2066 | 0.053 |
| 125 | 30 + 50 | 80 | 933 | 0.086 | 2058 | 0.039 |
| 126 | 30 + 50 | 80 | 471 | 0.170 | 2065 | 0.039 |
| 127$^d$ | 30 + 50 + 20 | 100 | 986 | 0.101 | 1529 | 0.065 |
| 128 | 20 + 20 + 20 + 20 | 80 | 633 | 0.126 | 2074 | 0.039 |

$^a$The values shown are concentrations of $SO_2$ remaining in sulfolene.
$^b$The average $Ni/SO_2$ for runs 101-108 was 0.364 g and for runs 109-128 was 0.173 g.
$^c$The average Ni/g sulfolene required for runs 101-108 was 0.097 g and for runs 109-128 was 0.047 g.
$^d$Run 127 did not contain a heel of sulfolene in the synthesis reactor.

Table III shows that addition of Raney nickel in small increments (runs 109-128) resulted in much smaller quantities (on the average 0.047 g nickel per g sulfolene) of catalyst required when compared with addition of a large initial increment (control runs 101-108 where the averaged nickel required was 0.097 g per g sulfolene). The results shown in Table III also demonstrate that the invention process improved the hydrogenation process by using less catalyst per gram sulfolene to be hydrogenated to sulfolane.

The results in Table III further show that even though the invention runs such as, for example, 109, 112, and 121-122 contained high levels of $SO_2$ in the sulfolene to be hydrogenated, the required catalyst per g sulfolene (last column, Table III) was substantially lower than the control runs. Again, these results demonstrate the advantage of the invention over the conventional process.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed is:

1. A process for preparing a sulfolane compound comprising: (1) reacting a conjugated diene with sulfur dioxide under conditions sufficient to synthesize a sulfolene compound whereby a mixture of said sulfolene compound and impurities comprising unreacted sulfur dioxide is produced; (2) transferring said mixture at a temperature in the range of about 55° C. to about 85° C. to an impurities removal reactor wherein said removal reactor already contains a solvent; (3) removing said impurities from said mixture to produce an impurities-reduced sulfolene compound; (4) transferring said impurities-reduced sulfolene compound to a hydrogenation reactor; (5) contacting said impurities-reduced sulfolene compound with hydrogen, in the presence of a hydrogenation catalyst, under sufficient hydrogenation conditions to produce said sulfolane compound.

2. A process according to claim 1 further comprising recovering said sulfolane compound.

3. A process according to claim 1 wherein said transferring in step (2) is carried out at a temperature in the range of about 58° C. to about 80° C.

4. A process according to claim 3 wherein said temperature is in the range of 60° C. to 76° C.

5. A process according to claim 1 wherein said conjugated diene has the formula of R—C(R)=C(R)—C(R)=C(R)—R; wherein each R can be the same or different and is independently selected from the group consisting of hydrogen, hydroxyl radical, and a hydrocarbyl radical, wherein said hydrocarbyl radical is selected from the group consisting of akyl, alkenyl, aryl, cycloalkyl, cycloalkenyl, aralkyl, alkaryl, alkylcycloalkyl, and combinations thereof.

6. A process according to claim 5 wherein said conjugated diene is selected from the group consisting of 1,3-butadiene, 2-methyl-1,3-butadiene, 2,3-dimethyl-1,3-butadiene, 2,3-diethyl-1,3-butadiene, 3,4-dimethyl-2,4-hexadiene, 2,4-dodecadiene, 2-methyl-1,3-hexadiene, 4-ethyl-1,3-hexadiene, 1-cyclopentyl-1,3-pentadiene, 1-(1-cyclohexene-1-yl)-1,3-butadiene, 2-phenyl-1,3-butadiene, 3-benzyl-1,3-pentadiene, 3-p-tolyl-1,3-pentadiene, and their homologues, and mixtures thereof.

7. A process according to claim 6 wherein said conjugated diene is 1,3-butadiene.

8. A process according to step (3) of claim 1 comprising removing said impurities under an elevated pressure in the range of from about 5 psig to about 500 psig for about 10 minutes to about 10 hours.

9. A process according to claim 8 wherein said pressure is in the range of from 20 psig to 100 psig.

10. A process according to step (3) of claim 1 further comprising, contemporaneous with said removing, sparging an inert gas to said mixture.

11. A process according to claim 10 wherein said inert gas is nitrogen.

12. A process according to claim 1 wherein said solvent is selected from the group consisting of water, an alcohol, a sulfone, an organic amide, and mixtures thereof.

13. A process according to claim 12 wherein said solvent is water.

14. A process according to step (5) of claim 1 wherein said hydrogenation catalyst is added to said hydrogenation reactor of step (4) of claim 1 in about 2 to about 10 increments wherein each incremental addition is about 10% to about 50% of total hydrogenation catalyst required which is the amount of hydrogenation catalyst necessary to substantially convert all sulfolene compounds in said hydrogenation reactor to sulfolane compounds.

15. A process for preparing a sulfolane compound comprising: (1) reacting a conjugated diene with sulfur dioxide at a temperature in the range of from about 60° C. to about 120° C. under a pressure in the range of from about 20 psig to about 300 psig for about 2 hours to about 24 hours whereby a mixture of sulfolene compound and impurities comprising unreacted sulfur dioxide is produced; wherein said conjugated diene is selected from the group consisting of 1,3-butadiene, 2-methyl-1,3-butadiene, 2,3-dimethyl-1,3-butadiene, 2,3-diethyl-1,3-butadiene, 3,4-dimethyl-2,4-hexadiene, 2,4-dodecadiene, 2-methyl-1,3-hexadiene, 4-ethyl-1,3-hexadiene, 1-cyclopentyl-1,3-pentadiene, 1-(1-cyclohexene-1-yl)-1,3-butadiene, 2-phenyl-1,3-butadiene, 3-benzyl-1,3-pentadiene, 3-p-tolyl-1,3-pentadiene, and their homologues, and mixtures thereof; (2) transferring said mixture at a temperature in the range of from about 58° C. to about 80° C. to an impurities removal reactor wherein said reactor already contains a solvent selected from the group consisting of water, methanol, ethanol, propanol, isopropanol, butanol, pentanol, sulfolane, N-methyl-2-pyrrolidone, N,N'-dimethylformamide, and mixtures thereof; (3) contemporaneous with sparging an inert gas, removing said impurities under a pressure in the range of from about 10 psig to about 300 psig to produce an impurities-reduced sulfolene compound; (4) transferring said impurities-reduced sulfolene compound to a hydrogenation reactor; (5) contacting said impurities-reduced sulfolene compound with hydrogen, in the presence of a hydrogenation catalyst which is added to said hydrogenation reactor in about 2 to about 10 increments wherein each incremental addition is about 10% to about 50% of total hydrogenation catalyst required, under hydrogenation conditions sufficient to produce said sulfolane compound.

16. A process for producing sulfolane comprising: (1) contacting 1,3-butadiene with sulfur dioxide at 65° C. to 80° C. under 30 psig to 120 psig to produce a mixture of sulfolene and impurities comprising unreacted sulfur dioxide; (2) transferring at 60° C. to 76° C. said mixture to an impurities removal reactor; (3) contemporaneous with sparging nitrogen gas, removing the impurities under 20 psig to 100 psig to produce an impurities-reduced sulfolene; (4) transferring said impurities-reduced sulfolene to a hydrogenation reactor; (5) contacting said impurities-reduced sulfolene compound with hydrogen, in the presence of a hydrogenation catalyst which is added to said hydrogenation reactor in about 2 to about 10 increments wherein each incremental addition is about 10% to about 50% of total hydrogenation catalyst required, under hydrogenation conditions sufficient to produce said sulfolene compound.

* * * * *